(12) United States Patent
Almeida Leñero et al.

(10) Patent No.: US 7,511,178 B2
(45) Date of Patent: Mar. 31, 2009

(54) PROCESS OF PREPARING ETHYLENE GLYCOL

(75) Inventors: Karina Quetzaly Almeida Leñero, Amsterdam (NL); Eit Drent, Amsterdam (NL); Roelof Van Ginkel, Amsterdam (NL); Robert Ian Pugh, Nottingham (GB)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 12/208,149

(22) Filed: Sep. 10, 2008

(65) Prior Publication Data
US 2009/0012333 A1 Jan. 8, 2009

Related U.S. Application Data

(62) Division of application No. 10/583,109, filed as application No. PCT/EP2004/053492 on Dec. 15, 2004, now Pat. No. 7,449,607.

(30) Foreign Application Priority Data
Dec. 16, 2003 (EP) ................... 03257883

(51) Int. Cl.
*C07C 31/18* (2006.01)
*C07C 29/14* (2006.01)
(52) U.S. Cl. ..................... 568/852; 568/862
(58) Field of Classification Search ............... 568/852, 568/862
See application file for complete search history.

(56) References Cited

U.S. PATENT DOCUMENTS

| 3,050,531 | A | 8/1962 | Epstein et al. | 260/340.7 |
| 4,414,421 | A | 11/1983 | Drent | 568/462 |
| 4,608,444 | A | 8/1986 | Jacobson | 568/462 |
| 2003/0092935 | A1 | 5/2003 | Ahlers | 562/522 |

FOREIGN PATENT DOCUMENTS

| EP | 0331512 | 9/1989 |
| WO | 01/85661 | 11/2001 |

OTHER PUBLICATIONS

International Search Report PCT/EP2004/053492 dated Apr. 27, 2005.
Drent, Eite: "Opportunities in Homogeneous Catalysis", Pure & Appl. Chem., vol. 62, No. 4, pp. 661-669; 1990.

*Primary Examiner*—Sikarl A Witherspoon

(57) ABSTRACT

The invention provides a process of preparing glycolaldehyde by reacting formaldehyde with hydrogen and carbon monoxide in the presence of a catalyst composition which is based on, a) a source of rhodium, and b) a ligand of general formula $R^1P\text{—}R^2$(I), wherein $R^1$ is a bivalent radical that together with the phosphorous atom to which it is attached is an optionally substituted 2-phospha-tricyclo[3.3.1.1{3,7}]-decyl group, wherein from 1 to 5 of the carbon atoms has been replaced by a heteroatom, and wherein $R^2$ is a monovalent radical which is an optionally substituted hydrocarbyl group having from 1 to 40 carbon atoms; a catalyst composition of use in said process; and a process of preparing ethylene glycol from the glycolaldehyde thus prepared.

7 Claims, No Drawings

US 7,511,178 B2

PROCESS OF PREPARING ETHYLENE GLYCOL

REFERENCE TO PRIOR APPLICATIONS

This application is a divisional of U.S. patent application Ser. No. 10/583,109, having a 35 U.S.C. 371 date of Apr. 9, 2007, now U.S. Pat. No. 7,449,607, which was filed as an International Application having a PCT No. of PCT/EP2004/053492, filed Dec. 15, 2004, claiming priority from European Application Ser. No. 03257883.3, filed Dec. 16, 2003, now abandoned, the entire disclosures of which are hereby incorporated by reference in their entireties.

FIELD OF THE INVENTION

The present invention relates to a process of preparing glycolaldehyde and a process of preparing ethylene glycol from the glycolaldehyde thus prepared.

BACKGROUND OF THE INVENTION

The reaction of an unsaturated substrate with carbon monoxide and hydrogen is known as hydroformylation. It has been disclosed in the past that glycolaldehyde, which is a useful intermediate for the preparation of ethylene glycol, may be prepared by a hydroformylation reaction of formaldehyde employing a rhodium catalyst. However, the preparation of glycolaldehyde in this way is hindered in that the rhodium catalyst also promotes hydrogenation of formaldehyde to methanol, lowering glycolaldehyde yields.

Attempts have been made to suppress methanol production and increase selectivity to the glycolaldehyde product and in this regard it has been found that good yields of glycolaldehyde can be achieved by use of rhodium catalysts containing aryl-substituted phosphine ligands such as triphenylphosphine, optionally in combination with protonoic acids (e.g. see Pure & Appl. Chem., Vol. 62, No. 4, pp. 661-669, 1990). However, such aryl-substituted ligands suffer from the disadvantage that they are unstable in the reaction conditions, lessening their effectiveness.

A further limitation on this method of preparing glycolaldehyde, in particular when it is to be used as an intermediate in the preparation of ethylene glycol, is that good results are only obtained when using para-formaldehyde in non-aqueous conditions and that use of the cheaper aqueous formaldehyde (formaline) gives lower conversion and selectivity to glycolaldehyde. This is thought to be due to the instability of the catalyst in aqueous conditions. Indeed, the difficulty in hydroformylating aqueous formaldehyde represents a major obstacle to the commercialisation of this approach for the production of ethylene glycol.

European patent application EP-A-0331512 reviews the use of a rhodium-phosphine ligand complex, wherein the phoshine ligand is a triorganophoshine, in the hydroformylation of aqueous formaldehyde to glycolaldehyde, which can then be used to prepare ethylene glycol.

A process has now been developed for hydroformylating formaldehyde that is based on the use of a rhodium catalyst and a specific form of phosphine ligand. The process has performance advantages when compared to known rhodium catalysts having aryl-substituted phosphine ligands. Moreover, the catalysts of the present invention are more stable in aqueous conditions than catalysts containing aryl-substituted phosphine ligands, and may readily be used to convert aqueous formaldehyde to glycolaldehyde.

SUMMARY OF THE INVENTION

The present invention provides a process of preparing glycolaldehyde which comprises reacting formaldehyde with hydrogen and carbon monoxide in the presence of a catalyst composition which is based on
 a) a source of rhodium, and
 b) a ligand of general formula $$R^1P\text{-}R^2 \tag{I}$$

wherein $R^1$ is a bivalent radical that together with the phosphorous atom to which it is attached is an optionally substituted 2-phospha-tricyclo[3.3.1.1{3,7}]-decyl group, wherein from 1 to 5 of the carbon atoms has been replaced by a heteroatom, and wherein $R^2$ is a monovalent radical which is an optionally substituted hydrocarbyl group having from 1 to 40 carbon atoms.

DETAILED DESCRIPTION OF THE INVENTION

The catalyst composition of the present invention requires a source of rhodium. Convenient sources of rhodium include rhodium salts of mineral acids, such as salts of sulphuric acid, nitric acid and phosphoric acid; salts of sulphonic acids, such as methane sulphonic acid and para-toluenesulphonic acid; and salts of carboxylic acids, in particular those having up to 6 carbon atoms, such as acetic acid, propionic acid and trifluoroacetic acid. Alternatively, the source of rhodium may contain rhodium in a zero-valent form, complexed by ligands such as carbon monoxide, acetylacetonates and phosphine ligands. The source of rhodium metal may contain a mixture of anions and uncharged ligands, e.g. as in $Rh.Cl(CO)_2$ or $Rh(acac)(CO)_2$.

In the ligand of general formula (I), $R^1$ represents a bivalent radical that together with the phosphorus atom to which it is attached is an optionally substituted 2-phospha-tricyclo[3.3.1.1{3,7}]decyl group, wherein from 1 to 5 of the carbon atoms has been replaced by a heteroatom.

Tricyclo[3.3.1.1{3,7}]decane is the systematic name for a compound more commonly known as adamantane. Therefore, for ease of reference, in the present description the optionally substituted 2-phospha-tricyclo[3.3.1.1{3,7}decyl group, or a derivative thereof, may be referred to as a "2-PA" group (as in 2-phosphadamantyl group).

In the ligands employed in the present invention, from 1 to 5 of the carbon atoms in the "2-PA" group have been replaced by a heteroatom. Examples of heteroatoms that may conveniently be used are oxygen and sulphur atoms, oxygen atoms being preferred. The from 1 to 5 carbon atoms replaced by heteroatoms are preferably those located at positions 4, 6, 8, 9, or 10 of the "2-PA" group. Most preferably 3 carbon atoms of the "2-PA" group have been replaced by heteroatoms, preferably at the 6, 9 and 10 positions.

Preferably, the "2-PA" group is substituted on one or more of the 1, 3, 5 or 7 positions with a monovalent radical of up to 20 atoms, preferably a radical comprising 1 to 10 carbon atoms and more preferably 1 to 6 carbon atoms. Examples of suitable monovalent radicals include methyl, ethyl, propyl, phenyl, and 4-dodecylphenyl groups, methyl and ethyl groups being preferred. More preferably, the "2-PA" group is substituted on each of the 1, 3, 5 and 7 positions. Most preferably the substituents on each of the 1, 3, 5 and 7 positions are identical.

Ligands that have given particularly good results in the present invention are those wherein the bivalent radical $R^1$ together with the phosphorous atom to which it is attached is a 2-phospha-1,3,5,7-tetralkyl-6,9,10-trioxa-tricyclo
[3.3.1.1{3,7}]-decyl group, of the formula:

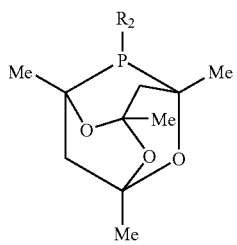

In the ligand of general formula (I), $R^2$ is a monovalent radical which is an optionally substituted hydrocarbyl group having from 1 to 40 carbon atoms. The hydrocarbyl groups may be substituted or unsubstituted, straight or branched chain, saturated or unsaturated; preferred such hydrocarbyl groups being alkyl, cycloalkyl, aryl, alkaryl and aralkyl groups. Where the hydrocarbyl group is substituted, substituents which the hydrocarbyl group may conveniently carry may be independently selected from one or more of halogen atoms (e.g. fluorine or chlorine), alkoxy, alkenyloxy, aryloxy, hydroxy, dialkylamido, diarylamido, alkylthio, arylthio, alkylsuphonyl, alkylsulphinyl, alkoxycarbonyl, dialkylamino and diarylamino groups. Herein as substituents suitably an alkyl moiety has from 1 to 4 carbon atoms, an alkenyl moiety has from 2 to 4 carbon atoms, and an aryl group has from 6 to 12 carbon atoms, and is especially phenyl. Preferred substituents are dialkylamido and diarylamido groups.

In a first preferred embodiment, the process of the present invention employs a ligand wherein the monovalent radical $R^2$ is an alkyl group having in the range of from 4 to 34 carbon atoms. Preferably, the alkyl group $R^2$ of this embodiment comprises at least 6 carbon atoms, most preferably at least 10, especially at least 12, carbon atoms; and preferably up to 28 carbon atoms, more preferably up to 22 carbon atoms. The alkyl group may be linear or branched, however it will preferably be linear. The ligands of this embodiment are preferred as they display a high conversion to glycol aldehyde and may enhance stability of the catalyst. They perform particularly well in the hydroformylation of formaldehyde in non-aqueous conditions.

Ligands that may be conveniently used in the present invention according to the first preferred embodiment include 2-phospha-2-hexyl-1,3,5,7-tetramethyl-6,9,10-trioxa-tricyclo[3.3.1.1{3,7}]-decane, 2-phospha-2-octyl-1,3,5,7-tetramethyl-6,9,10-trioxa-tricyclo[3.3.1.1{3,7}]-decane, 2-phospha-2-dodecyl-1,3,5,7-tetramethyl-6,9,10-trioxa-tricyclo [3.3.1.1{3,7}]-decane, and 2-phospha-2-icosyl-1,3,5,7-tetramethyl-6,9,10-trioxa-tricyclo[3.3.1.1{3,7}]-decane.

In a second preferred embodiment, the process of the present invention employs a ligand wherein the monovalent radical $R^2$ is of general formula $$—R^3—C(O)NR^4R^5 \quad (II)$$

wherein $R^3$ is an alkylene group and $R^4$ and $R^5$ independently represent an alkyl, cycloalkyl, aryl or alkaryl group, or $R^4$ and $R^5$ together represent a bivalent bridging group. Conveniently, alkylene group $R^3$ is a methylene, ethylene, propylene or butylene group, most conveniently an ethylene group. Preferably, $R^4$ and $R^5$ independently represent an aryl group, for example phenyl; or an alkyl group, preferably an alkyl group having from 1 to 22 carbon atoms. Examples of alkyl groups that may conveniently be used include methyl, ethyl, propyl, butyl, and pentyl groups. Ligands wherein $R^2$ is of general formula (II) are preferred as they display an excellent conversion to glycolaldehyde and are particularly advantageous for hydroformylation reactions performed with aqueous formaldehyde.

Ligands that may be conveniently used in the present invention according to the second preferred embodiment include 2-phospha-2-(ethyl-N,N-diethylamido)-1,3,5,7-tetramethyl-6,9,10-trioxa-tricyclo[3.3.1.1{3,7}]-decane, 2-phospha-2-(ethyl-N,N-diphenylamido)-1,3,5,7-tetramethyl-6,9,10-trioxa-tricyclo[3.3.1.1{3,7}]-decane, and 2-phospha-2-(ethyl-N,N-dimethylamido)-1,3,5,7-tetramethyl-6,9,10-trioxa-tricyclo[3.3.1.1{3,7}]-decane.

The ligands of general formula (I) may be prepared by coupling an optionally substituted 2-phospha-tricyclo [3.3.1.1{3,7}]-decane, wherein from 1 to 5 of the carbon atoms has been replaced by a heteroatom, with a suitable $R^2$ group precursor. The 2-phospha-tricyclo[3.3.1.1{3,7}]-decane may conveniently be prepared by analogous chemistry to that described in U.S. Pat. No. 3,050,531, wherein for instance 2-phospha-1,3,5,7-tetramethyl-6,9,10-trioxa-tricyclo[3.3.1.1{3,7}]-decane is prepared by reacting 2,4-pentanedione with phosphine in the presence of hydrochloric acid. Similar chemistry is also discussed in chapter 3 of "PRECIOUS METAL COMPLEXES OF SOME NOVEL FUNCTIONALISED SECONDARY AND TERTIARY PHOSPHINES" by Ms. Joanne H Downing (thesis submitted to the University of Bristol on November 1992).

Examples of $R^2$ group precursors include compounds of formula $R^2$—X, wherein X is a halide, for example a chloride or bromide, which may conveniently be used when preparing ligands of general formula (I) wherein $R^2$ is an alkyl group; for example by reaction of an $R^2$—X compound with 2-phospha-1,3,5,7-tetramethyl-6,9,10-trioxa -tricyclo[3.3.1.1{3, 7}]-decane or its borane adduct. Alternatively, when $R^2$ is of general formula —$R^3$—C(O)NR$^4$R$^5$ (II), the $R^2$ group precursor may conveniently be an N,N-disubstituted alkenylamide. For example, ligands wherein $R^3$ is an ethylene group and $R^4$ and $R^5$ are alkyl groups may be prepared by reaction of a dialkyl-acrylamide with a "2-PA" group in the presence of acid, e.g. acetic acid. Other ligands according to the present invention may be prepared by analogous chemistry, as will be understood by those skilled in the art.

The catalyst compositions employed in the present invention may optionally comprise a source of anions c) as a further catalyst component. Preferred anions are anions of protic acids having a pKa (measured at 18° C. in water) of less than 6, preferably less than 4. The anions derived from these acids do not or only weakly coordinate with the rhodium, by which it is meant that little or no covalent interaction occurs between the anion and the rhodium. Catalysts comprising such anions exhibit good activity.

Examples of suitable anions include those derived from Bronsted acids, such as phosphoric acid and sulphuric acid; as well as anions derived from sulphonic acids e.g. methanesulphonic acid, trifluoromethane sulphonic acid, p-toluenesulphonic acid and 2,4,6-trimethylbenzenesulphonic acid; and anions derived from carboxylic acids, e.g. 2,4,6-trimethylbenzoic acid, 2,4,6 tri-isopropylbenzoic acid; 9-antracene carboxylic acid and halogenated carboxylic acids such as trifluoroacetic acid 2,6-dichlorobenzoic acid, and 2,6 bis(trifluoromethyl)benzoic acid. Particularly good results have been obtained using alkyl-substituted benzoic acids, especially $C_1$ to $C_4$ alkyl-substituted benzoic acids, as a source of anions.

Also suitable are complex anions, such as the anions generated by the combination of a Lewis acid such as $BF_3$, $B(C_6F_5)_3$, $AlCl_3$, $SnF_2$, $Sn(CF_3SO_3)_2$, $SnCl_2$ or $GeCl_2$, with a protic acid, preferably having a pKa of less than 5, such as a sulphonic acid, e.g. $CF_3SO_3H$ or $CH_3SO_3H$ or a hydrohalogenic acid such as HF or HCl, or a combination of a Lewis acid with an alcohol. Examples of such complex anions are $BF_4$—, $SnCl_3$—, $[SnCl_2 \cdot CF_3SO_3]$— and $PF_6$—.

The molar ratio of carbon monoxide to hydrogen supplied to the process of the present invention is not critical and may vary over a wide range, for example of from 5:95 to 95:5, preferably of from 30:70 to 80:20. However, it is generally preferred to use a gas stream in which the molar ratio of $CO:H_2$ is at least 1:1, since this minimises the formation of methanol. The process is preferably conducted under pressure, conveniently in the range of from 5 to 200 bar (0.5 to 20 MPa) and preferably in the range of from 10 to 50 bar (1 to 5 MPa). Higher pressures may be used, however they are generally considered uneconomical. Inert gasses may also be present in the gas stream but as this leads to an increase in total pressure it is generally undesirable.

The hydroformylation reaction of the present invention may be conveniently carried out at moderate temperatures, preferably in the range of from 22 to 180° C., more preferably 50 to 130° C. The use of a temperature as low as possible commensurate with the desired reaction rate is preferred since at higher temperatures the glycolaldehyde product is susceptible to undergo side reactions, e.g. aldol condensation reactions.

The reaction time for the process of the invention is of course dependent on the temperature and pressure conditions utilised. It has been generally found that the reaction time may be in the range of from 1 to 10 hours, preferably 1 to 6 hours, especially 2 to 5 hours.

The quantity in which the catalyst system is used in the present invention is not critical and may vary within wide limits. However, the amount of mole atom of rhodium metal per mole of formaldehyde will preferably be in the range of from 1:1 to $1:10^6$, more preferably from 1:10 to $1:10^5$, and even more preferably from 1:100 to $1:10^4$.

For the preparation of catalyst systems employed in the present invention, the amount of ligand of general formula (I) is generally applied in an excess to the amount of rhodium, expressed as moles of ligand per mole atom of rhodium. Typically the amount of ligand is selected such that per mole atom of rhodium 1 to 20 moles of ligand are present. However, for a preferred catalyst system the molar amount of ligand per mole of rhodium is preferably in the range of from 2 to 10, more preferably in the range of from 2 to 5. When present the amount of the anion source c), whilst not critical, may range from 1 to 500, preferably from 1 to 150, and more preferably from 1 to 20 moles per mole atom of rhodium.

The process of the present invention may be carried out in the presence of a solvent. Examples of solvents that may conveniently be used include nitriles, pyridine, substituted or unsubstituted ureas, for example N,N,N',N'-tetrasubstituted ureas, and substituted or unsubstituted amides, for example N,N-disubstituted amides.

The formaldehyde may be introduced into the reaction system in any suitable form, or it may be generated in situ. A convenient source of formaldehyde is para-formaldehyde. Further, it is an advantageous feature of the present invention that good results are achieved when aqueous formaldehyde is employed as the source of formaldehyde. Accordingly, in a preferred process according to the present invention the source of formaldehyde is aqueous formaldehyde.

Where the source of formaldehyde is aqueous formaldehyde it is further preferred that the process is performed in a reaction medium comprising an aqueous phase and an organic phase, wherein the organic phase and aqueous phase are immiscible at 22° C. For the avoidance of doubt, by immiscible it is meant that on standing at 22° C. the organic phase and aqueous phase will separate into two distinct layers. A reaction medium comprising an aqueous phase and an organic phase is preferred as on completion of the reaction the catalyst will reside in the organic phase, whilst the glycolaldehyde product will reside in the aqueous phase, and thus the product may readily be separated from the catalyst by phase separation. Such an approach is possible in the present invention as the catalyst compositions are more stable in aqueous conditions than known catalysts based on aryl-substituted phosphine ligands.

Where the process is performed in a reaction medium comprising an aqueous phase and an organic phase, the solvent of the organic phase may conveniently be a water-immiscible amide solvent. Examples of water-immiscible amide solvents that can be employed in the present invention are those comprising long chain alkyl moieties and includes N-alkyl-2-pyrrolidones wherein the alkyl group comprises at least 7 carbon atoms, preferably in the range of from 8 to 20 carbon atoms, N,N-dialkyl-acetamides, in which each alkyl group has in the range of from 1 to 10 carbon atoms, preferably from 1 to 6 carbon atoms, and N,N-diaryl-acetamides, preferably N,N-diphenylacetamide. Examples of water-immiscible amide solvents that have given particularly good results when employed in the present invention include N-octyl-pyrrolidone and N,N-dibutyl-acetamide.

A particularly preferred embodiment of the present invention is wherein the process is performed in a reaction medium comprising an aqueous phase and an organic phase comprising a water-immiscible amide solvent, and wherein in the ligand of general formula $R^1P$—$R^2$ (I), the monovalent radical $R^2$ is of general formula —$R^3$—$C(O)NR^4R^5$ (II).

The rhodium-containing catalyst compositions described herein above were specifically developed for use in the process of the present invention.

Catalyst compositions of this type fall within the wide-ranging definition of metal-ligand complexes described in US-A-2003/0092935 for the hydroformylation of olefins such as α-olefins, internal olefins, and internal branched olefins. The preferred catalyst compositions for use in the process of the present invention are distant from the preferred metal-ligand complexes of US-A-2003/0092935 and display an excellent activity in the hydroformylation of formaldehyde, a very different substrate, in both non-aqueous and aqueous conditions. Catalyst compositions in which the monovalent radical $R^2$, of the ligand (I), is of general formula —$R^3$—$C(O)NR^4R^5$ (II) perform especially well in aqueous conditions for example when formalin is used as the substrate, or when water is present in the reaction medium. Accordingly, the present invention further provides a catalyst composition obtainable by combining a) a source of rhodium, b) a ligand of general formula

$$R^1P\text{—}R^2 \qquad (I)$$

wherein $R^1$ is a bivalent radical that together with the phosphorous atom to which it is attached is an optionally substituted 2-phospha-tricyclo[3.3.1.1{3,7}]-decyl group, wherein from 1 to 5 of the carbon atoms has been replaced by a heteroatom, and wherein $R^2$ is a monovalent radical which is an optionally substituted alkyl group having from 10 to 40 carbon atoms, or is, preferably, of the general formula —$R^3$—$C(O)NR^4R^5$, wherein $R^3$ is an alkylene group and $R^4$ and $R^5$ independently represent an alkyl, cycloalkyl, aryl or alkaryl group or $R^4$ and $R^5$ together represent a bivalent bridging group, and optionally c) a source of anions. Within these definitions of $R^2$, preferred catalyst compositions as described herein before with respect to the process of the present invention are similarly preferred as the catalyst composition of the invention.

An important use of glycolaldehyde is its conversion to ethylene glycol and the present invention still further provides a process of preparing ethylene glycol by hydrogenating glycolaldehyde prepared by the hydroformylation process described herein above.

Hydrogenation catalysts of use in the conversion of glycolaldehyde to ethylene glycol are well known in the art, for example palladium, platinum or nickel catalysts, often in heterogeneous form. Where glycolaldehyde is prepared in non-aqueous conditions, the selected hydrogenation catalyst may be added directly to the reaction mixture resulting from the preparation of glycolaldehyde with no work-up procedure, and gaseous hydrogen introduced. Alternatively, the reaction mixture may be worked-up before the glycolaldehyde is hydrogenated, e.g. by extraction with a suitable solvent such as water or ethylene glycol itself, and the resulting solution then hydrogenated in conventional manner. This approach is particularly convenient when the glycolaldehyde is prepared from aqueous formaldehyde in a reaction medium comprising an aqueous phase as has now been made possible by means of the present invention.

The invention will be further understood from the following illustrative examples.

Ligand Synthesis

The following examples, which were performed under an atmosphere of purified argon using standard Schlenk techniques, illustrate a typical preparation of a ligand according to the present invention wherein (i) $R^2$ is an alkyl group (2-phospha-2-icosyl-1,3,5,7-tetramethyl -6,9,10-trioxa-tricyclo [3.3.1.1{3,7}]-decane), and (ii) $R^2$ is of general formula (II) (2-phospha-2-(ethyl-N,N-dimethylamido) -1,3,5,7-tetramethyl-6,9,10-trioxa -tricyclo[3.3.1.1{3,7}]-decane).

(i) Synthesis of 2-Phospha-2-Icosyl-1,3,5,7-tetramethyl -6,9,10-Trioxa-Tricyclo[3.3.1.1{3,7}]-decane.

A borane adduct of 2-phospha-1,3,5,7-tetramethyl-6,9,10-trioxa-tricyclo[3.3.1.1{,3,7}]-decane was prepared by adding $BH_3.THF$ (70 ml of 1M solution in THF) to a solution of 2-phospha-1,3,5,7-tetramethyl-6,9,10-trioxa -tricyclo [3.3.1.1{3,7}]-decane(60 mmol) in THF at 0° C. The reaction mixture was allowed to warm to room temperature and stir for two hours after which time the solvent was removed in vacuo to yield the borane adduct.

To a solution of this adduct (16 mmol in THF) a solution of hexyl-lithium (6.4 ml, 2.5M in hexane) was added at a temperature of –70° C. and the reaction mixture allowed to slowly warm to –20° C. over a period of 1 hour. After recooling to –70° C., a solution of 1-bromo-icosane (16 mmol in THF) was added. The reaction mixture was then allowed to warm to ambient temperature and stirred for 2 hours before diethylamine (3 ml) was added and the reaction mixture then refluxed for 12 hours. On completion of the reaction the solvent was removed in vacuo. The product was then isolated by solvent extraction in dichloromethane-toluene and water, the toluene fractions being evaporated to leave a solid residue that was washed with methanol to yield 2-phospha -2-icosyl-1,3,5,7-tetramethyl-6,9,10-trioxa -tricyclo[3.3.1.1{3,7}]-decane(96%).

(ii) Synthesis of 2-Phospha-2-(Ethyl-N,N-Dimethylamido) - 1,3,5,7-Tetramethyl-6,9,10-Trioxa-Tricyclo[3.3.1.1{3,7}]-decane.

2-Phospha-1,3,5,7-tetramethyl-6,9,10-trioxa -tricyclo [3.3.1.1{3,7}]-decane(40 mmol) and N, N dimethylacrylamide (100 mmol) were introduced into a Schlenk-tube containing a mixture of toluene and acetic acid, and heated to a temperature of 115° C. After 18 hours the reaction mixture was cooled to 80° C. and the solvents evaporated in vacuo. The residue was then dissolved in triethylamine and the mixture heated to a temperature of 100° C. for 2.5 hours after which the resulting homogeneous mixture was cooled to ambient temperature. The product was then isolated by solvent extraction with toluene and water, the toluene fractions being evaporated to yield 2-phospha-2-(ethyl-N,N-dimethylamido) -1,3,5,7-tetramethyl-6,9,10-trioxa -tricyclo [3.3.1.1{3,7}]-decane(79%).

Hydroformylation of Formaldehyde

The following examples were performed in a magnetically stirred 250 ml autoclave. The autoclave was charged with reactants and solvent after which air was removed and the autoclave pressurised with carbon monoxide and hydrogen, each to a partial pressure of 30 bar (3 MPa). The contents of the autoclave were then heated to reaction temperature. Upon completion of the reaction, the contents were cooled and the conversion of formaldehyde, and yield of glycolaldehyde, was determined by means of gas-liquid chromatography using di-ethylene glycol dimethylether as an internal standard. All ligands were prepared using analogous chemistry to that described for ligands (i) and (ii) above.

EXAMPLE 1

("2-PA"-$C_{20}$ Ligand in Non-Aqueous Conditions)

The autoclave was charged with 0.17 mol of formaldehyde, in the form of para-formaldehyde, 62 ml (0.58 mol) of N-methyl-pyrrolidone, 0.25 mmol of rhodiumdicarbonylacetonylacetone (Rh(acac)(CO)$_2$), 0.50 mmol of 2-phospha-2-icosyl-1,3,5,7-tetramethyl-6,9,10-trioxa-tricyclo[3.3.1.1{3,7}]-decane, and 9.1 mmol of trimethylbenzoic acid. The contents of the autoclave were then heated to a temperature of 110° C. and maintained at that temperature for 2 hours.

Conversion of formaldehyde was 100% and the yield of glycolaldehyde, calculated on formaldehyde intake, was 76%. The initial reaction rate was calculated by measurement of the pressure drop to be 595 mol CO/mol Rh.h.

EXAMPLE 2

("2-PA"—$C_{20}$ Ligand in Aqueous Conditions)

The autoclave was charged with 0.17 mol of formaldehyde, in the form of para-formaldehyde, 35 ml (0.22 mol) of dibutyl-acetamide, 25 ml of demineralised water, 0.25 mmol of Rh(acac) (CO)$_2$, 0.53 mmol of 2-phospha-2-icosyl-1,3,5,7-tetramethyl-6,9,10-trioxa -tricyclo[3.3.1.1{3,7}]-decane, and 9.1 mmol of trimethylbenzoic acid. The contents of the autoclave were heated to a temperature of 110° C. and maintained at that temperature for 5 hours.

Conversion of formaldehyde was 64% and the yield of glycolaldehyde in the two-phase reaction product, calculated on formaldehyde intake, was 45%. The initial reaction rate was calculated by measurement of the pressure drop to be 115 mol CO/mol Rh.h

EXAMPLE 3

("2-PA"—$CH_2CH_2C(O)NMe_2$ Ligand in Non-Aqueous Conditions)

The autoclave was charged with 0.18 mol of formaldehyde, in the form of para-formaldehyde, 23 ml (0.15 mol) of di-sec-butyl-acetamide, 0.25 mmol of Rh(acac)(CO)$_2$, 0.49 mmol of 2-phospha-2-(ethyl-N,N-dimethylamido) -1,3,5,7-tetramethyl-6,9,10-trioxa -tricyclo[3.3.1.1{3,7}]-decane, and 9.1 mmol of trimethylbenzoic acid. The contents of the autoclave were then heated to a temperature of 100° C. and maintained at that temperature for 3 hours.

Conversion of formaldehyde was 72% and the yield of glycolaldehyde in the single-phase reaction product, calculated on formaldehyde intake, was 69%. The initial reaction rate was calculated by measurement of the pressure drop to be 275 mol CO/mol Rh.h.

EXAMPLE 4

("2-PA"—$CH_2CH_2C(O)NMe_2$ Ligand in Non-Aqueous Conditions)

The autoclave was charged with 0.25 mol of formaldehyde, in the form of para-formaldehyde, 35 ml (0.26 mol) of N,N'-dimethylpropyleneurea, 0.10 mmol of $Rh(acac)(CO)_2$, 0.20 mmol of 2-phospha-2-(ethyl-N,N-dimethylamido) -1,3,5,7-tetramethyl-6,9,10-trioxa -tricyclo[3.3.1.1{3,7}]-decane, and 3.1 mmol of trimethylbenzoic acid. The contents of the autoclave were then heated to a temperature of 90° C. and maintained at that temperature for 5 hours.

Conversion of formaldehyde was 73% and the yield of glycolaldehyde in the single-phase reaction product, calculated on formaldehyde intake, was 71%. The initial reaction rate was calculated by measurement of the pressure drop to be 595 mol CO/mol Rh.h.

EXAMPLE 5

("2-PA"—$CH_2CH_2C_{18}$ Ligand in Non-Aqueous Conditions)

The autoclave was charged with 0.25 mol of formaldehyde, in the form of para-formaldehyde, 35 ml (0.26 mol) of N,N'-dimethylpropyleneurea, 0.10 mmol of $Rh(acac)(CO)_2$, 0.20 mmol of 2-phospha-2-octyl-1,3,5,7-tetramethyl-6,9,10-trioxa-tricyclo[3.3.1.1{3,7}]-decane, and 3.1 mmol of trimethylbenzoic acid. The contents of the autoclave were then heated to a temperature of 90° C. and maintained at that temperature for 5 hours.

Conversion of formaldehyde was 69% and the yield of glycolaldehyde in the single-phase reaction product, calculated on formaldehyde intake, was 66%. The initial reaction rate was calculated by measurement of the pressure drop to be 518 mol CO/mol Rh.h.

EXAMPLE 6

("2-PA"—$CH_2CH_2C(O)NMe_2$ Ligand in Aqueous Conditions)

The autoclave was charged with 0.15 mol of formaldehyde, in the form of a formaline solution (37% formaldehyde in water), 37 ml (0.22 mol) of dibutyl-acetamide, 7.5 ml of demineralised water, 0.49 mmol of $Rh(acac)(CO)_2$, 0.96 mmol of 2-phospha-2-(ethyl-N,N-dimethylamido) -1,3,5,7-tetramethyl-6,9,10-trioxa- tricyclo[3.3.1.1{3,7}]-decane, and 9.1 mmol of trimethylbenzoic acid. The contents of the autoclave were heated to a temperature of 90° C. and maintained at that temperature for 5 hours.

Conversion of formaldehyde was 90% and the yield of glycolaldehyde in the two-phase reaction product, calculated on formaldehyde intake, was 90%. The initial reaction rate was calculated by measurement of the pressure drop to be 170 mol CO/mol Rh.h.

EXAMPLE 7

("2-PA"—$CH_2CH_2C(O)NPh_2$ Ligand in Aqueous Conditions)

The autoclave was charged with 0.15 mol of formaldehyde, in the form of a formaline solution (37% formaldehyde), 37 ml (0.22 mol) of dibutyl-acetamide, 7.5 ml of demineralised water, 0.44 mmol of $Rh(acac)(CO)_2$, 0.89 mmol of 2-phospha-2-(ethyl-N,N-diphenylamido) -1,3,5,7-tetramethyl-6,9,10-trioxa-tricyclo[3.3.1.1{3,7}]-decane, and 9.1 mmol of trimethylbenzoic acid. The contents of the autoclave were heated to a temperature of 110° C. and maintained at that temperature for 3 hours.

Conversion of formaldehyde was 100% and the yield of glycolaldehyde in the two-phase reaction product, calculated on formaldehyde intake, was 52%. The initial reaction rate was calculated by measurement of the pressure drop to be 180 mol CO/mol Rh.h.

COMPARATIVE EXAMPLE A ($PPh_3$ Ligand in Non-Aqueous Conditions)

The autoclave was charged with 0.17 mol of formaldehyde, in the form of para-formaldehyde, 37 ml (0.24 mol) of dibutyl-acetamide, 0.25 mmol of $Rh(acac)(CO)_2$, 0.52 mmol of triphenylphosphine, and 9.3 mmol of trimethylbenzoic acid. The contents of the autoclave were then heated to a temperature of 90° C. and maintained at that temperature for 10 hours.

Conversion of formaldehyde was 61% and the yield of glycolaldehyde in the single-phase reaction product, calculated on formaldehyde intake, was 40%. The initial reaction rate was calculated by measurement of the pressure drop to be 75 mol CO/mol Rh.h

COMPARATIVE EXAMPLE B ($PPh_3$ Ligand in Aqueous Conditions)

The autoclave was charged with 0.17 mol of formaldehyde, in the form of para-formaldehyde, 37 ml (0.22 mol) of dibutyl-acetamide, 12.5 ml of demineralised water, 0.25 mmol of $Rh(acac)(CO)_2$, 0.52 mmol of triphenylphosphine, and 9.1 mmol of trimethylbenzoic acid. The contents of the autoclave were heated to a temperature of 90° C. and maintained at that temperature for 10 hours.

Conversion of formaldehyde was 54% and the yield of glycolaldehyde in the two-phase reaction product, calculated on formaldehyde intake, was 25%. The reaction rate was calculated by measurement of the pressure drop to be 51 mol CO/mol Rh.h.

COMPARATIVE EXAMPLE C (9-Icosyl-9-Phosphabicyclo[3.3.1]nonane Ligand in Aqueous Conditions)

The autoclave was charged with 0.17 mol of formaldehyde, in the form of para-formaldehyde, 37 ml (0.19 mol) of N-octyl-pyrrolidone, 25 ml of demineralised water, 0.25 mmol of $Rh(acac)(CO)_2$, 0.52 mmol of 9-icosyl -9-phosphabicyclo [3.3.1]nonane, and 9.1 mmol of trimethylbenzoic acid. The contents of the autoclave were heated to a temperature of 110° C. and maintained at that temperature for 5 hours.

Conversion of formaldehyde was 17% and the yield of glycolaldehyde in the two-phase reaction product, calculated on formaldehyde intake, was 6%.

COMPARATIVE EXAMPLE D (9-$CH_2CH_2C(O)NMe_2$-9-Phosphabicyclo[3.3.1]nonane Ligand in Aqueous Conditions)

The autoclave was charged with 0.17 mol of formaldehyde, in the form of para-formaldehyde, 37 ml (0.22 mol) of dibutyl-acetamide, 25 ml of demineralised water, 0.25 mmol of $Rh(acac)(CO)_2$, 0.50 mmol of 9-phospha-9-(ethyl-N,N-dimethylamido-bicyclo[3.3.1]nonane, and 9.1 mmol of trimethylbenzoic acid. The contents of the autoclave were then heated to a temperature of 110° C. and maintained at that temperature for 5 hours.

Conversion of formaldehyde was 3% and the yield of glycolaldehyde in the two-phase reaction product, calculated on formaldehyde intake, was 0%.

The above examples demonstrate that catalyst compositions according to the present invention display a superior performance to comparative compositions containing a triphenylphosphine ligand under both aqueous and non-aqueous conditions (e.g. compare Examples 1 and 3 with Comparative Example A, and Examples 2 and 4 with Comparative Example B), and to catalysts based on other forms of bicyclic phosphine-containing ligand (see Comparative Examples C and D). Moreover, from Examples 4 and 5 it can also be seen that catalyst compositions of general formula (I) wherein $R^2$ is of general formula —$R^3$—$C(O)NR^4R^5$ continue to display a good level of performance even under aqueous conditions.

Hydrogenation to Ethylene Glycol

To demonstrate the ease with which glycolaldehyde prepared according to the present invention may be converted to ethylene glycol, an aqueous phase separated from a hydroformylation reaction performed under conditions analogous to those of Example 2 ("2-PA"—$C_{20}$ ligand in aqueous conditions) was treated with Raney Nickel slurry. The aqueous phase (25 ml, 9.5% wt glycolaldehyde) was mixed with Raney Nickel slurry (2 ml) and stirred for 15 hours at a temperature 40° C., then treated with hydrogen at a pressure of 50 bar (5 Mpa). The conversion from glycolaldehyde to ethylene glycol was 90%.

What is claimed is:

1. A process for preparing ethylene glycol comprising:
    forming glycolaldehyde by reacting formaldehyde with hydrogen and carbon monoxide in the presence of a catalyst composition comprising
        a) a source of rhodium, and
        b) a ligand of general formula $$R^1P—R^2 \qquad (I)$$

wherein $R^1$ is a bivalent radical that together with the phosphorous atom to which it is attached is an optionally substituted 2-phospha-tricyclo[3.3.1.1{3,7}]-decyl group, wherein from 1 to 5 of the carbon atoms have been replaced by a heteroatom, and wherein $R^2$ is a monovalent radical which is an optionally substituted hydrocarbyl group having from 1 to 40 carbon atoms; and
    hydrogenating said glycolaldehyde.

2. The process as claimed in claim 1, wherein the catalyst composition further comprises c) a source of anions.

3. The process as claimed in claim 1, wherein bivalent radical $R^1$ together with the phosphorous atom to which it is attached is a 2-phospha-1,3,5,7-tetralkyl-6,9,10-trioxa-tricyclo[3.3.1.1{3,7}]-decyl group.

4. The process as claimed in claim 1, wherein monovalent radical $R^2$ is an alkyl group having from 4 to 34 carbon atoms.

5. The process as claimed in claim 1, wherein monovalent radical $R^2$ is of the general formula $$—R^3—C(O)NR^4R^5 \qquad (II)$$

wherein $R^3$ is an alkylene group and $R^4$ and $R^5$ independently represent an alkyl, cycloalkyl, aryl or alkaryl group, or $R^4$ and $R^5$ together represent a bivalent bridging group.

6. The process as claimed in claim 1, wherein the formaldehyde is aqueous formaldehyde and the reaction is performed in a reaction medium comprising an aqueous phase and an organic phase, wherein the organic phase and aqueous phase are immiscible at 22° C.

7. The process as claimed in claim 6, wherein the organic phase comprises a water-immiscible amide solvent.

* * * * *